United States Patent [19]

Tsuaki

[11] Patent Number: 4,546,916
[45] Date of Patent: Oct. 15, 1985

[54] HUMIDIFIER

[75] Inventor: Hajime Tsuaki, Kani, Japan

[73] Assignee: Tokyo Shibaura Denki Kabushiki Kaisha, Kawasaki, Japan

[21] Appl. No.: 585,163

[22] Filed: Mar. 1, 1984

[30] Foreign Application Priority Data

Mar. 15, 1983 [JP] Japan .................................. 58-42742

[51] Int. Cl.$^4$ ............................................. G05D 22/00
[52] U.S. Cl. ................................ 236/44 A; 236/44 E; 73/336.5
[58] Field of Search ............................ 73/29, 73, 336.5; 324/65 R; 340/602; 338/35; 236/44 R, 44 E, 44 A, 44 C

[56] References Cited

U.S. PATENT DOCUMENTS

| | | | |
|---|---|---|---|
| 4,146,775 | 3/1979 | Kirchner et al. | 236/44 R X |
| 4,350,286 | 9/1982 | Sutoh et al. | 236/44 A |
| 4,419,021 | 12/1982 | Terada et al. | 73/336.5 |

FOREIGN PATENT DOCUMENTS

| | | | |
|---|---|---|---|
| 1548 | 1/1980 | Japan . | |
| 37444 | 4/1981 | Japan | 236/44 E |
| 1545481 | 5/1979 | United Kingdom . | |

Primary Examiner—Harry B. Tanner
Attorney, Agent, or Firm—Cushman, Darby and Cushman

[57] ABSTRACT

A humidifier for controlling ambient moisture includes a moisture sensor having a capacitor component and a resistor component which may vary in response to the ambient moisture, a pseudo AC square-wave generator for supplying a square-wave source voltage to the sensor which is the sum of two separate square-wave voltages, and a moisture detector section to which a sensor output voltage and a reference voltage electrically representing an objective moisture value are supplied. When the sensor output voltage reaches the stable potential after the transient phenomenon to be caused by the sensor capacitor component, the moisture detector section compares the stable voltage with the above reference voltage, thereby performing the moisture detection which faithfully corresponds to the sensor resistor component.

19 Claims, 9 Drawing Figures

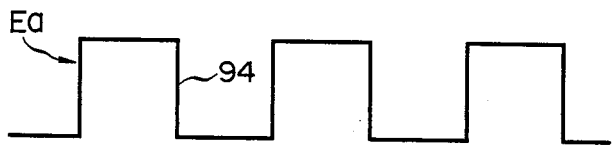
F I G. 2A
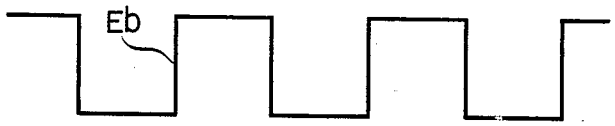
F I G. 2B
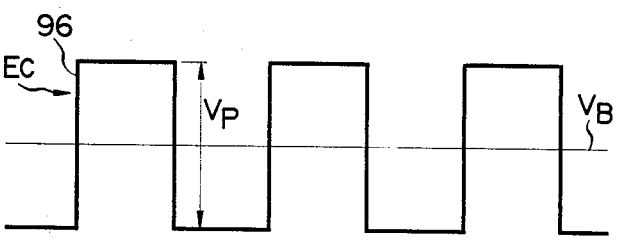
F I G. 2C
F I G. 2D
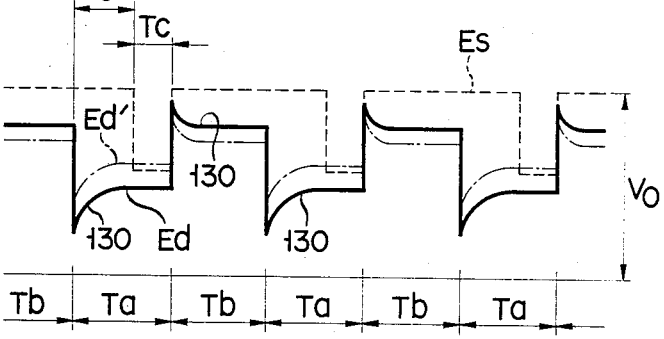
F I G. 2E

HUMIDIFIER

BACKGROUND OF THE INVENTION

The present invention relates in general to a moisture detecting apparatus for automatically detecting the ambient moisture on the basis of an output signal from an electric resistance moisture sensor and, more particularly, to a moisture controller for automatically controlling the ambient moisture on the basis of an output signal from an electric resistance moisture sensor in order to optimize the ambient moisture in a room and the like.

It has already been known that the actual moisture level is detected using a moisture sensor which varies with the resistance value of itself depending upon a change in ambient moisture. As a moisture sensor, for example, a device is employed which is made of a porous ceramic material and whose resistance value continuously changes due to the water molecule adsorption phenomenon of the porous ceramic. Conventionally, a reference voltage is applied across the terminals of the moisture sensor of the above-mentioned type, thereby obtaining a moisture detection voltage signal responsive to the ambient moisture level. In this case, when a DC power voltage is directly applied to the moisture sensor, the porous ceramic moisture sensor, which adsorbs water molecules, will have made its moisture detection ability worse due to a so-called "electrolytic corrosion" phenomenon. Therefore, an AC voltage is conventionally applied across the terminals of the above-mentioned sensor.

However, in this case, another critical problem is caused whereby the moisture detection accuracy of the moisture sensor may deteriorate. This is because the moisture sensor of the above-mentioned type includes a capacitance component as an equivalent circuit, causing a noise voltage which is due to this capacitance component being added to the moisture detection voltage signal which is obtained on the basis of the applied AC voltage and of the sensor resistance which varies in accordance with the ambient moisture.

SUMMARY OF THE INVENTON

It is an object of the present invention to provide a new and improved moisture detecting apparatus which accurately detects the ambient moisture, thereby enabling the operational reliability to be improved.

According to an ambient moisture sensing apparatus of the present invention, an electrical moisture sensor is employed, having a capacitor component and a resistor component which varies in response to the actual ambient moisture. A voltage which alternately varies between first and second potentials at predetermined intervals is applied to the sensor as a source voltage thereof. A detector device is provided for receiving a sensor output voltage which varies depending upon the source voltage and a reference voltage electrically representing the objective humidity value. The sensor output voltage includes the transient voltage component which transiently varies due to the sensor capacitor component, and the stable voltage component which is produced thereafter and which faithfully corresponds to the sensor resistor component. The detector device compares only this stable voltage component with the reference voltage, thereby generating a comparison result signal responsive to the magnitude relationship between these potentials.

BRIEF DESCRIPTION OF THE DRAWINGS

The present invention is best understood with reference to the accompanying drawings, in which:

FIGS. 2A to 2E show waveform diagrams of the signals generated at the main parts of the ultrasonic humidifier shown in FIG. 1;

DETAILED DESCRIPTION OF THE PREFERRED EMBODIMENTS

Figure 1:
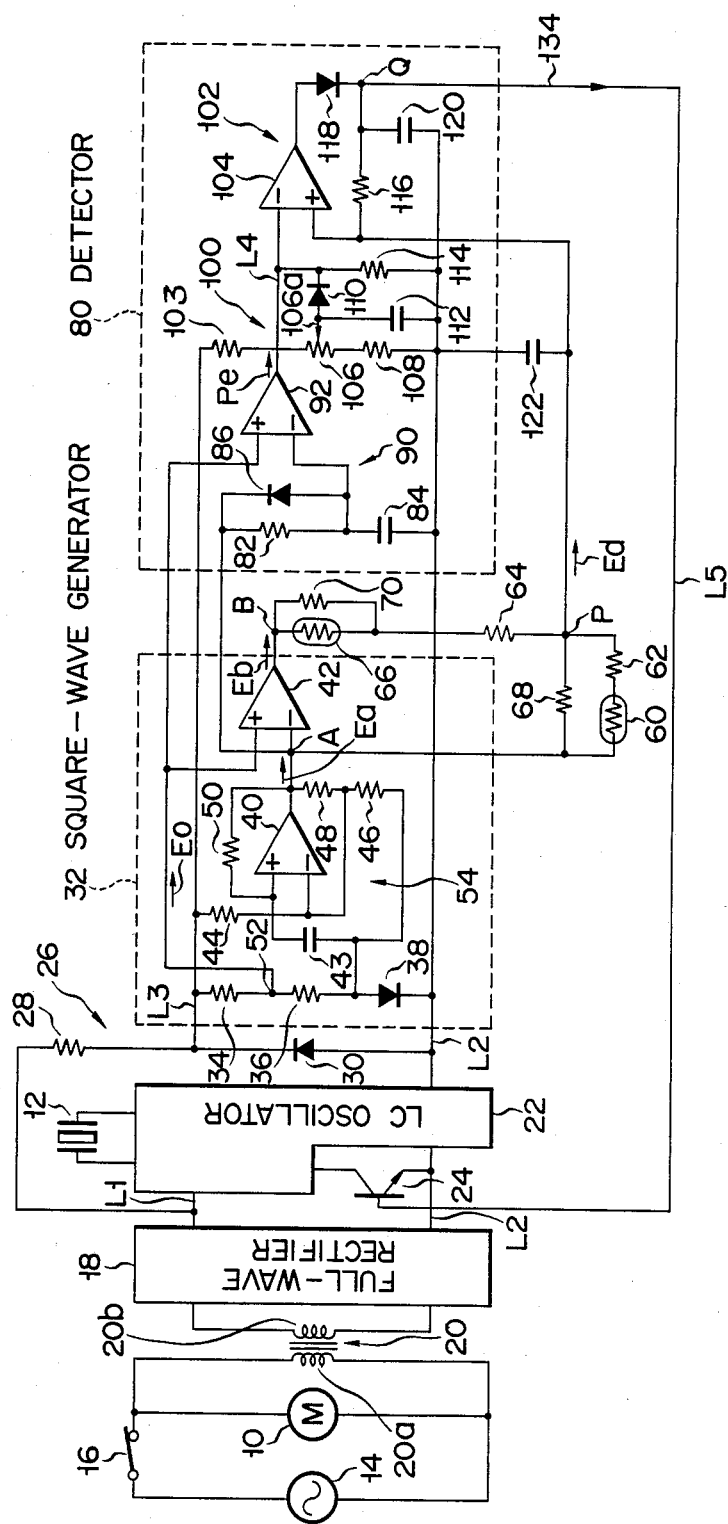
FIG. 1 is a circuit diagram illustrating the circuit configuration of an ultrasonic humidifier in accordance with one embodiment of the present invention.

Referring to FIG. 1, there is illustrated a whole circuit configuration of an ultrasonic humidifier as one preferred embodiment of the present invention. The humidifier has a fan motor 10 and an ultrasonic transducer 12. The fan motor 10 is connected to an AC power source 14 through a main switch 16. The fan motor 10 is further connected to a full-wave rectifying circuit 18 through a primary side coil 20a and a secondary coil 20b of a step-down transformer 20. The full-wave rectifier 18 includes a well-known bridge circuit consisting of, for example, four diodes (not shown) and a smoothing capacitor (not shown). This rectifier 18 serves to full-wave rectify an AC power source voltage which is supplied from the AC power source 14 and which was dropped by the transformer 20, thereby supplying a suitable DC voltage through voltage lines L1 and L2 to an oscillator 22 at the next stage. In FIG. 1, a fan motor 10 is provided to forcedly shoot out of the main body (not shown) of the humidifier a fog consisting of water molecules which is produced due to the ultrasonic vibration of a ultrasonic transducer 12. The ultrasonic transducer 12 is fixed on the inner bottom surface of a water tank (not shown), in the known manner.

In order to drive the ultrasonic transducer 12, the oscillator 22 includes a known LC oscillating circuit (not shown) having an oscillating transistor, an inductive element such as a choke coil, and a capacitive element such as a capacitor. The oscillating transistor is Darlington-connected to a switching transistor 24. In other words, the collector and emitter of the oscillating transistor included in the LC oscillator 22 are connected to the collector and emitter of the switching transistor 24, respectively. In this embodiment, when the transistor 24 is operative or conductive, the oscillating transistor of the oscillator 22 is rendered non-operative or non-conductive, thereby forcedly stopping the oscillating operation of the LC oscillator 22.

A constant voltage circuit 26 consisting of a series circuit of a resistor 28 and a Zener diode 30 is connected between lines L1 and L2. Therefore, the constant DC voltage is supplied between voltage lines L3 and L2 to which the cathode and anode of the Zener diode 30 are connected, respectively.

A square-wave generating circuit 32 is connected between the lines L3 and L2. In the circuit 32, a series circuit consisting of resistors 34, 36 and a diode 38 is connected between the lines L3 and L2, thereby constituting a voltage-divider which suitably divides the output DC voltage from the constant voltage circuit 26. The square-wave generator 32 includes two operational amplifiers 40 and 42. The first operational amplifier 40 has a non-inverting input connected to line L3 through a time-constant determining capacitor 43 and the resistors 34 and 36. An inverting input of the first operational amplifier 40 is connected to line L3 through a resistor 44 and is also connected to line L2 through a resistor 46 and the diode 38. A resistor 48 is provided between the inverting input and the output of the operational amplifier 40, while a resistor 50 is connected between the output and the non-inverting input of the first amplifier 40. The output of the first operational amplifier 40 is connected to an inverting input of the second operational amplifier 42. The second amplifier 42 has a non-inverting input connected to a common juncture 52 between the two resistors 34 and 36.

The circuit components consisting of the first operational amplifier 40, capacitor 43, and resistors 44, 46, 48, 50 constitute a square-wave oscillator 54 which generates a square-wave voltage signal Ea as illustrated in FIG. 2A. The signal Ea of FIG. 2A is supplied to the inverting input of the second operational amplifier 42. At this time, a suitable constant DC voltage $E_0$ is supplied from the common juncture 52 to the non-inverting input of the second operational amplifier 42. Consequently, as shown in FIG. 2B, a square-wave output signal Eb, having the phase in which the above-mentioned square-wave voltage signal Ea was inverted by 180°, is output from this second operational amplifier 42. A square-wave voltage Ec, shown in FIG. 2C, is output from circuit points A and B (see FIG. 1) corresponding to the output terminals of the square-wave generator 32, i.e., from the inverting input and the output of the second operational amplifier 42. As is obvious from FIG. 2C, the peak-to-peak voltage value Vp of this square-wave voltage Ec is equal to twice that of the voltage signal Ea. Therefore, assuming that the potential at point B is the reference potential, the pulsate voltage component of the square-wave voltage Ec respectively varies high and low in the positive and negative directions by only the peak-to-peak voltage value of the pulsate voltage signal Ea or Eb.

An electric resistance moisture sensor 60, resistors 62, 64 and a thermistor 66 are connected in series between the output terminals A and B of the above square-wave generator 32. A resistor 68 is connected in parallel with the serial circuit of the moisture sensor 60 and resistor 62, while another resistor 70 is provided in parallel to the thermistor 66.

Figure 3:
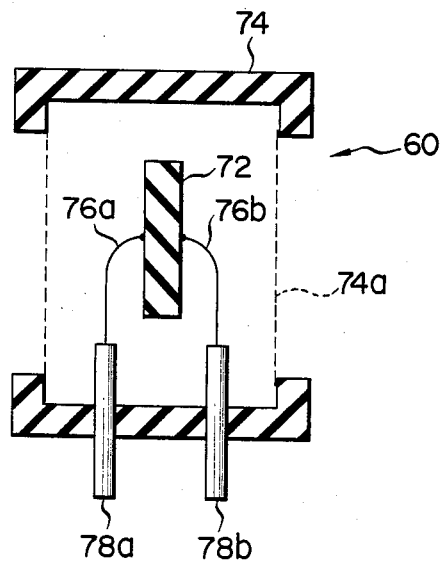
FIG. 3 is a diagram showing the sectional view of a moisture sensor used in the humidifier of FIG. 1.
Figure 4:
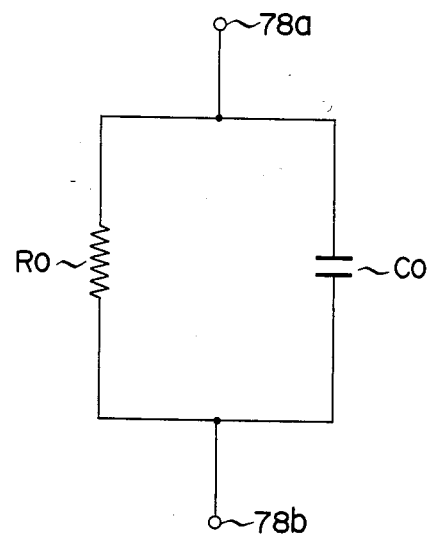
FIG. 4 is a diagram showing an equivalent circuit of the moisture sensor, the circuit including a resistor and capacitor connected in parallel with each other.

The above moisture sensor 60 may vary its electric resistance value depending upon the magnitude of the ambient moisture so as to detect the circumferential ambient moisture in the room where the ultrasonic humidifier of FIG. 1 is disposed. The moisture sensor 60 generates a detection signal Ed representing the magnitude of the actual ambient moisture as shown in FIG. 2E, when the voltage signal of FIG. 2C is applied thereto. The internal configuration of this moisture sensor 60 is illustrated schematically in FIG. 3. The moisture sensor 60 is constituted in such a manner that a porous sintered body 72, made of ceramic, is disposed in a cylindrical casing 74 having at its circumferential side surface a ventilation mesh member 74a, and lead wires 76a and 76b, which are respectively drawn out from the opposed side surfaces of the porous sintered body 72, are each connected to terminals 78a and 78b. A decrease in the resistance value between the terminals 78a and 78b to be caused in association with the water molecule adsorption phenomenon of the porous sintered body 72 corresponds to the ambient moisture. Therefore, the ambient moisture can be sensed due to the voltage change characteristic at point P (common juncture of the resistors 64 and 68) in FIG. 1. In addition, as shown in FIG. 4, the equivalent circuit of this moisture sensor 60 corresponds to the circuit configuration in which a resistor component $R_0$, which varies depending upon the ambient moisture and a peculiar capacitor component $C_0$, are connected in parallel. The previously mentioned thermistor 66, connected in series with such a moisture sensor 60, is provided to compensate the output voltage characteristic of the moisture sensor 60 (i.e., output voltage characteristic at point P) in accordance with the ambient temperature. The resistors 62 and 68 are provided to linearize the output voltage characteristic of the moisture sensor 60, while the resistor 70 is provided for matching the characteristic of the thermistor 66.

A detecting circuit 80 is provided at the post stage of the square-wave generator 32. The detector 80 includes a charging resistor 82 and a time constant-determining capacitor 84, which are connected in series between line L2 and the inverting input of the second operational amplifier 42 (i.e., the circuit point A). A discharge control diode 86 is connected in parallel with the resistor 82. A delay circuit 90 is constituted by these circuit components 82, 84, 86 and an operational amplifier 92. An anode of the diode 86 is connected to an inverting input of the operational amplifier 92, which has a non-inverting input connected to the non-inverting input of the second operational amplifier 42 included in the square-wave generator 32 and the common juncture 52 of the resistors 34 and 36 included therein. Therefore, the operational amplifier 92 receives at its non-inverting input the constant DC voltage $E_0$ to be supplied from the above common juncture 52. At the same time, the amplifier 92 receives at its inverting input the charging voltage of the capacitor 84 included in the delay circuit 90.

In the delay circuit 90, when the square-wave voltage Ea is generated from the first operational amplifier 40 included in the square-wave generator 32, this voltage Ea is charged through the resistor 82 in the capacitor 84, whereby the voltage across the capacitor 84 increases accordingly. During this interval, the delay circuit 90 outputs a high level voltage signal. When a constant time (i.e., delay time to be unconditionally determined by the time constant which is decided by the resistor 82 and the capacitor 84) passes from the beginning of charging in the capacitor 84, the increasing charging voltage level of the capacitor 84 exceeds the constant DC voltage $E_0$, which is supplied from the constant voltage circuit 26. At this time, the output voltage from the delay circuit 90, included in the detector 80, is inverted from a high level to a low level. Thereafter, when the square-wave voltage Ea to be output from the first operational amplifier 40 of the square-wave generator 32 falls, as shown at a reference numeral 94 in FIG. 2A, the charges accumulated in the capacitor 84 are rapidly discharged through the diode 86. Due to this, the output voltage of the operational amplifier 92 is again inverted so as to return to the high level. As a result, the delay circuit 90 generates a delay voltage pulse component Pe having a low voltage level as shown in FIG. 2D, after a predetermined delay time τ has passed from the instant 96 when the square-wave voltage Ec was changed to have the high potential level.

The detector 80 further includes a moisture level setting circuit section 100 for presetting a reference humidity value, and a comparator circuit section 102 which has an operational amplifier 104 serving as a voltage comparator.

The moisture level setting circuit section 100 contains a voltage dividing resistor 103, a variable resistor 106 which may vary its resistance linearly, and a resistor 108. These resistors 103, 106 and 108 are connected in series to each other and are provided between lines L3 and L2. A slidable terminal 106a of the variable resistor 106 is connected through a diode 110 to a line L4 which is connected to both the output of the operational amplifier 92 and the inverting input of the other operational amplifier 104. The anode and cathod of this diode 110 are connected to the line L2 through a capacitor 112 and a resistor 114, respectively.

In the comparator circuit section 102 included in the detector 80, the non-inverting input of the operational amplifier 104 is directly connected to the previously-mentioned circuit point P, and at the same time it is fed-back to the output of the operational amplifier 104 through a resistor 116 and a diode 118 which serves as an output of the comparator circuit section 102. A common juncture Q of the resistor 116 and a cathode of the diode 118 is connected through a signal line L5 to a base electrode of the aforementioned switching transistor 24 connected to the LC oscillator 22. Furthermore, a capacitor 120 is connected between the above point Q and the line L2. The output voltage at point Q is smoothed by the capacitor 120. In addition, a noise preventing capacitor 122 is connected between the line L2 and point P.

The operation mode of the humidifier including therein the moisture detecting device as one embodiment of the present invention, which is constituted as described above, will now be described. When the power switch 16 is rendered conductive, a power source voltage is fed to the fan motor 10 by the AC power source 14, causing a fan (not shown) to be rotated. At the same time DC voltage is applied between lines L1 and L2, and a constant DC voltage is also applied between lines L2 and L3. The square-wave generator 32 is rendered operative in response to this supplied voltage, thereby generating the square-wave voltage Ec, whose waveform is as illustrated in the FIG. 2C, between two circuit points A and B of FIG. 1. This square-wave voltage Ec is applied to the series circuit consisting of the moisture sensor 60, and resistors 62 and 64. As described above, the resistance value of the moisture sensor 60 varies in response to the ambient moisture. Therefore, a moisture detection voltage signal Ed, which may vary its level in accordance with the resistance value of this moisture sensor 60, is generated from circuit point P of FIG. 1. The waveform of this voltage signal is indicated by the solid line in FIG. 2E.

As already described, the moisture sensor 60 equivalently includes the capacitor component $C_0$. As represented by the reference numeral 96 in FIG. 2C, the square-wave voltage Ec to be applied to the sensor 60 steeply rises around a potential $V_B$ at circuit point B at its central level. Consequently, as denoted at a reference numeral 130 in FIG. 2E, the transient voltage change (i.e., transient phenomenon of voltage), corresponding to the charging in the above capacitor component $C_0$, occurs in the moisture detection voltage signal Ed, to be output from the moisture sensor 60, whenever the voltage polarity of the square-wave component of the square-wave voltage Ec, which is applied to the moisture sensor 60, is inverted. The detection signal Ed becomes stable at predetermined voltage levels, responding to the variable resistance value $R_0$ of the moisture sensor 60, after the transient voltage change is caused by a capacitor component $C_0$. It should be noted that in a period Ta (i.e., an interval when the square-wave voltage Ea, which is input to circuit point A or the inverting input of the operational amplifier 42, has the pulse component at high voltage level; that is, an interval when the square-wave double voltage Ec, which is applied to the moisture sensor 60, holds a higher voltage level than the reference voltage $V_B$), the resistance value of this moisture sensor 60 becomes smaller as the ambient moisture becomes higher and, as a result, the stable potential level of the detection voltage Ed becomes higher. On the contrary, in an interval Tb (i.e., an interval when the square-wave voltage Eb, which is generated at circuit point B or the output of the operational amplifier 42, has the pulse component at high voltage level; that is, an interval when the square-wave double voltage Ec, which is applied to the moisture sensor 60, holds a lower voltage level than the reference voltage $V_B$), the resistance value of this moisture sensor 60 becomes smaller as the ambient moisture becomes higher and, as a result, the stable potential level of the detection voltage Ed becomes lower. The above moisture detection signal Ed is supplied to the non-inverting input of the operational amplifier 104 in the detector section 80.

Responding to the supply of the constant DC voltage $E_0$, the delay circuit 90 included in the detector section 80 is also rendered operative together with the square-wave generator 32. The delay pulse signal Pe, shown in FIG. 2D, is output to line L4 by this delay circuit 90. Under such a situation, if the voltage level of a moisture setting reference voltage signal $E_1$, generated from the moisture level setting circuit 100, has been set into the voltage level $V_0$ shown, e.g., in FIG. 2E, by controlling the resistance value of the variable resistor 106, a super-imposed voltage signal Es, which is obtained by adding the delay pulse signal Pe from the delay circuit 90 to the above-mentioned voltage signal $E_1$, appears at the above line L4. In this case, as is apparent from FIG. 2E, the detection voltage level is lower than the reference voltage level (Ed < Es). Thus, the operational amplifier 104 in the comparator circuit 102 generates a low level signal as a comparison result signal 134. This low level signal is supplied through the line L5 to the switching transistor 24. Since this transistor 24 is rendered non-conductive in response to the above-mentioned low level signal, this allows the LC oscillator 22 to start the oscillating operation. The ultrasonic transducer 12 is driven by the LC oscillator 22 serving to perform the oscillating operation, thereby permitting the humidifying or moistening operation to be executed. When the ambient moisture in the room where the present humidifier is installed increases due to continuation of such a moistening operation, the resistance value of the moisture sensor 60 decreases in response to this increased moisture. The level of the moisture detection voltage signal Ed, output from the moisture sensor 60, increases in the interval Ta (indicated in FIG. 2E) and decreases in the other interval Tb. When the detection signal Ed assumes a waveform state Ed′, illustrated by the alternate long and short dash line in FIG. 2E, (i.e., an interval when the detection voltage level Ed keeps the relationship in which it is higher than the reference setting voltage level Es (Ed>Es) in a detection signal level stable interval Tc corresponding to the pulse width of the delay pulse Pe), the operational amplifier 104 of the comparator circuit 102 generates a high level signal as the comparison result signal 134 only in this interval Tc. This high level signal is smoothed by the diode 118 and capacitor 120, so that the signal, which continuously maintains the high voltage level, is generated from circuit point Q of FIG. 1. The switching transistor 24 is rendered conductive in response to this continuous high voltage level signal. Therefore, the oscillating operation of the LC oscillator 22 is forcedly stopped, and the ultrasonic transducer 12 is made non-operative. As a result of this, the moistening operation of the present humidifier is stopped. Thereafter, when the ambient moisture decreases and again returns to the relationship of Ed<Es, the transistor 24 connected to the LC oscillator 22 is held to be in the OFF state by a similar operation as described before, and the moistening operation is restarted. Then, the on-off operation of the transistor 24 is similarly repeated, so that the ambient moisture is automatically controlled to the level set by the moisture level setting circuit 100.

According to the above embodiment, the pulsate DC voltage, i.e., square-wave voltage Ec having a proper duty ratio, is applied to the moisture sensor 60 for measuring the ambient moisture. The transient phenomenon to be caused by the capacitor component $C_0$, which is peculiarly included in this sensor 60, appears in the waveform of the detection voltage signal to be output responsive to the ambient moisture from the moisture sensor 60 to which this square-wave voltage Ec is applied. Consequently, the level of the detection voltage signal Ed varies and become unstable in a predetermined interval from the point of time when the potential level of the above square-wave voltage Ec steeply varies between the two values. According to the present invention, the delay circuit 90 is equipped at the front stage of the comparator circuit 102 for comparing the moisture detection signal level (Ed) with the reference voltage level (Es) representing the objective moisture value. The above reference voltage level Es is delayed by only the time $\tau$ which substantially corresponds to the interval when the level of the above detection signal Ed is made unstable by the capacitor component $C_0$ of sensor 60, and then this delayed voltage level Es is transmitted to the comparator circuit 102. Therefore, the comparison of the moisture detection voltage level Ed and the reference voltage level Es in this comparator circuit 102 is executed only when the transient phenomenon at the detection voltage level was finished and this detection voltage level became at the state (stationary state) in which it stably holds the voltage level that faithfully corresponds to the ambient moisture. It is possible, therefore, to completely eliminate the bad influence due to the capacitor component $C_0$, peculiarly in the moisture sensor 60 itself, from the moisture detecting operation. Thus, the moisture detection accuracy of the moisture sensor 60 can be improved. In addition, since the pulsate voltage is applied to the moisture sensor 60, it is possible to effectively suppress the undesirable occurrence of the electrolytic corrosion phenomenon of the sensor which conventionally occurred. Therefore, the ambient moisture can be accurately detected and the moisture detecting apparatus, having high operational reliability, can be realized.

Figure 5:
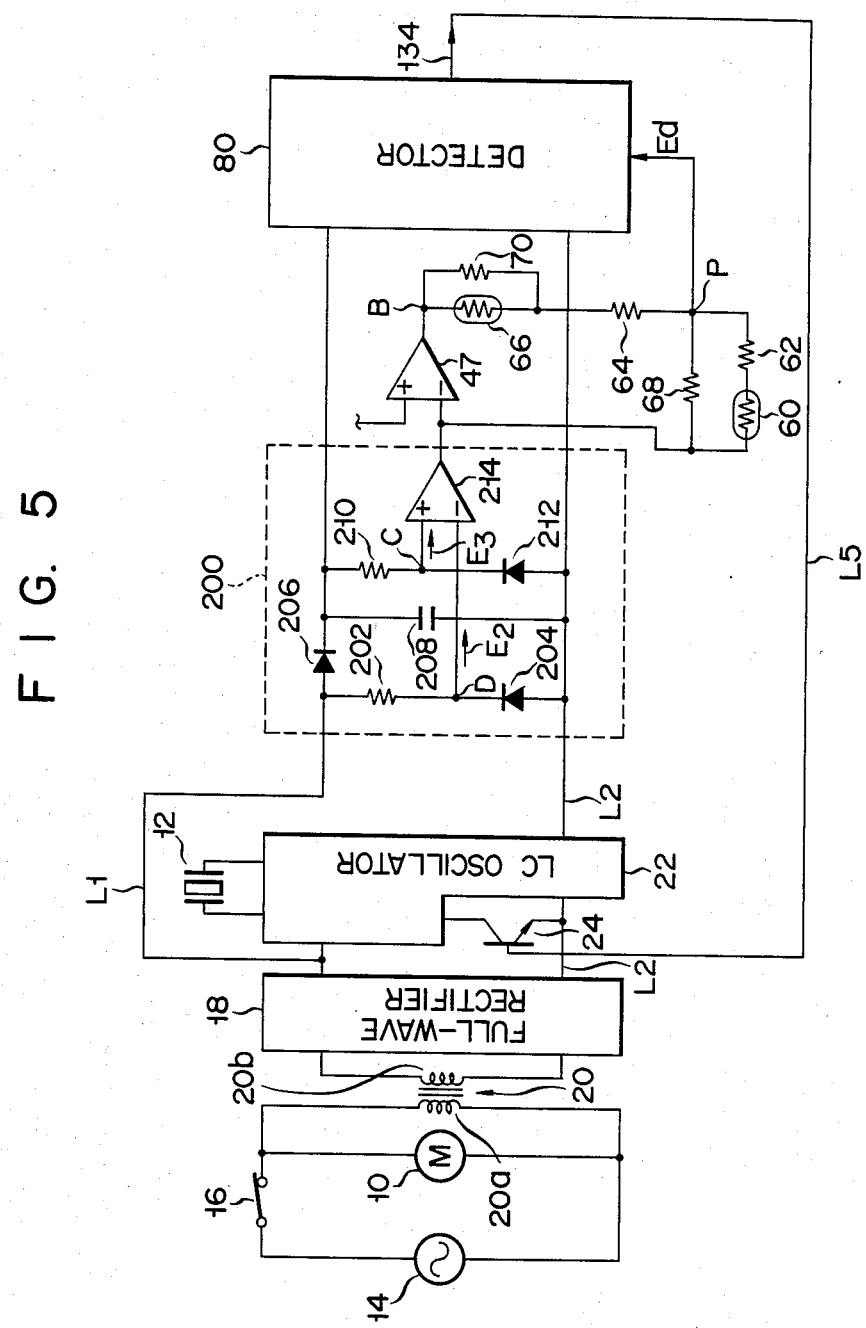
FIG. 5 is a circuit diagram illustrating the circuit configuration of an ultrasonic humidifier in accordance with another embodiment of the present invention.

FIG. 5 partially illustrates the main electric circuit of the humidifier as another embodiment of the present invention. With respect to this second embodiment, only the portion different from the above-described first embodiment will be described below. Namely, this second embodiment has a feature from the viewpoint that a waveform shaping circuit 200 is provided in place of the diode 38 and the square-wave oscillator 54 in the square-wave generator 32 of the first embodiment. In this waveform shaping circuit 200, a resistor 202 and a Zener diode 204 of the polarity shown in FIG. 5 are connected between lines L1 and L2. At the same time, a diode 206 of the polarity shown in the diagram is connected to the line L1, while a smoothing capacitor 208 is connected between lines L1 and L2. A resistor 210 and a Zener diode 212 of the polarity shown in the diagram are connected in parallel with this smoothing capacitor 208. Furthermore, the waveform shaping circuit 200 has an operational amplifier 214 and the non-inverting input terminal of this operational amplifier 214 is connected to point C (common juncture of the resistor 210 and Zener diode 212) in FIG. 5, while the inverting input terminal is connected to point D (common juncture of the resistor 202 and Zener diode 204) in FIG. 5. With such a constitution, the output terminal of the operational amplifier 214, as the output terminal of the waveform shaping circuit 200, is connected to the inverting input terminal of the operational amplifier 47 which serves as an inverting circuit.

In such a waveform shaping circuit 200, a wavy voltage $E_2$, which is analogous to the full-wave rectified waveform of the AC power source 14, is output from point D and, at the same time, a smoothed voltage $E_3$ at a constant level, of which the above-mentioned full-wave rectified waveform was smoothed through the diode 206 and smoothing capacitor 208, is output from point C. Due to this, the operational amplifier 214, for comparing the wavy voltage $E_2$ with the smoothed voltage Es, generates a square-wave voltage similar to that of FIG. 2A which rises only when there is the relationship of $E_2 < E_3$. Therefore, even in this embodiment, a similar action and effect as those in the first embodiment are obtained.

Although the present invention has been shown and described with respect to particular embodiments, various changes and modifications which are obvious to a person skilled in the art to which the invention pertains are deemed to lie within the spirit and scope of the invention.

What is claimed is:

1. An apparatus for detecting ambient moisture, comprising:
   moisture sensor means for outputting a sensor output signal in response to a source voltage, said output signal having a capacitor component and a resistor component which vary with changes in ambient moisture;
   square-wave generator means for supplying to said sensor a square-wave source voltage which alternately varies between first and second potentials at a predetermined period thereby constituting a pseudo AC source voltage, said generator means comprising first voltage generator means for generating a first square-wave voltage having a first amplitude, and second voltage generator means for generating a second square-wave voltage having a second amplitude, said second square-wave voltage being added to said first square-wave voltage with one of said first and second square-wave voltages used as a reference potential so as to define said pseudo AC source voltage; and detector means for receiving said sensor output signal and a reference voltage representative of an objective moisture value, said detector means including timer means for indicating a stable component included in said sensor output which occurs after a transient component thereof which varies due to said sensor capacitor component, said stable component accurately corresponding to said sensor resistor component, and including means for generating a moisture detection signal by comparing said stable component with said reference voltage.

2. An apparatus for controlling ambient moisture, comprising:

moisture sensor means for outputting a sensor output signal in response to a source voltage, said output signal having a capacitor component and a resistor component which vary with changes in the ambient moisture;

source voltage generator means for supplying to said sensor a square-wave source voltage which alternately varies between first and second potentials at a predetermined period thereby constituting a pseudo AC source voltage, said generator means comprising, first voltage generator means for generating a first square-wave voltage having a first amplitude, and second voltage generator means for generating a second square-wave voltage of a second amplitude, said first and second amplitudes being added together and with one of them used as a reference potential to produce said pseudo AC source voltage;

objective moisture value setting means for generating a reference voltage representative of an objective value of ambient moisture;

moisture detection means, connected to said sensor means and said objective moisture value setting means, for indicating a first stable voltage component included in said sensor means and which corresponds to said sensor means resistor component, said first voltage component being generated after a second transient voltage component which varies due to said sensor means capacitor component, and for comparing said first voltage component with said reference voltage to generate a comparison signal in accordance with their respective voltage magnitudes; and moisture control means, connected to said moisture detection means, for controlling ambient moisture in response to said comparison signal.

3. A method for detecting ambient moisture, comprising the steps of:

generating a first square-wave voltage having a first amplitude and a second square-wave voltage having a second amplitude which is added to the first square-wave voltage so as to produce a pseudo AC square-wave source voltage having as its amplitude the sum of the first and second amplitudes, said square-wave source voltage alternately varying between first and second potentials at a predetermined period;

supplying the square-wave source voltage to a moisture sensor having an output voltage based thereon with a capacitor component and a resistor component which vary in response to the ambient moisture;

producing a reference voltage electrically representing an objective value of the ambient moisture;

specifying a first stable voltage component included in the output voltage from said sensor which is generated after a second voltage component that transiently varies due to the sensor capacitor component, the first stable voltage accurately corresponding to the sensor resistor component; and comparing the first stable voltage component with the reference voltage to thereby accurately detect the ambient moisture.

4. The apparatus according to claim 1, wherein said detector means comprises:

first circuit means for generating said reference voltage defined as a pulsate voltage signal which is generated after said transient component of said sensor output has passed, said pulsate voltage signal being synchronized with the period of said pseudo AC source voltage and having a smaller pulse width than that of said stable component.

5. The apparatus according to claim 4, wherein said pulsate voltage signal has a pulse height which can vary in accordance with the setting of the objective moisture.

6. The apparatus according to claim 5, wherein said detector means further comprises:

second circuit means, connected to said sensor means and said first circuit means, for comparing said sensor output voltage with the pulse height of said pulsate voltage signal to output a comparison signal in response to the relative magnitude relationship between them as said detection signal.

7. The apparatus according to claim 6, wherein said first and second circuit means include a delay circuit and a comparator circuit, respectively.

8. The apparatus according to claim 1, wherein said detector means comprises:

first circuit means for generating said reference voltage defined as a pulsate voltage signal which is generated after said transient component of said sensor output, said pulsate voltage signal being synchronized with the period of said pseudo AC source voltage and having a smaller pulse width than that of said stable component.

9. The apparatus according to claim 8, wherein said pulsate voltage signal has a pulse height which can vary in accordance with the setting of the objective moisture.

10. The apparatus according to claim 9, wherein said detector means further comprises:

second circuit means, connected to said sensor means and said first circuit means, for comparing said sensor output voltage with the pulse height of said pulsate voltage signal to output a comparison signal responsive to the relative magnitude relationship between them as said detection signal.

11. The apparatus according to claim 10, wherein said first and second circuit means include a delay circuit and a comparator circuit, respectively.

12. The apparatus according to claim 2, wherein said moisture control means comprises:
   moisture increasing means for generating foggy water in response to said comparison signal, thereby increasing the ambient moisture.

13. The apparatus according to claim 12, wherein said moisture increasing means includes:
   ultrasonic transducer means for producing ultrasonic waves, thereby generating fog.

14. The apparatus according to claim 2, wherein said detection means comprises:
   first circuit means for generating said reference voltage as a pulsate voltage signal which is generated after said second voltage component, said pulsate voltage signal being synchronized with the period of said pseudo AC source voltage and having a smaller pulse width than that of said first voltage component.

15. The apparatus according to claim 14, wherein said detector means further comprises:
   second circuit means, connected to said sensor means and said first circuit means, for comparing said sensor output voltage with the pulse height of said pulsate voltage signal to output a detection signal in response to the relative magnitude relationship between them as said comparison signal.

16. The method according to claim 3, wherein said reference voltage includes:
   a pulsate voltage signal which is generated after the second voltage component and which is synchronized with the period of the pseudo AC source voltage and which has a smaller pulse width than the generating time of the first voltage component.

17. The method according to claim 16, wherein said pulsate voltage signal has a pulse height which can vary in accordance with the setting of the objective moisture.

18. The method according to claim 17, further comprising the step of:
   controlling the ambient moisture in accordance with the comparison of the first voltage component and the reference voltage.

19. The method according to claim 18, wherein said ambient moisture varying step comprises the step of:
   generating foggy water and adding it to the ambient moisture when the first voltage component is lower than the reference voltage.

* * * * *